United States Patent
Wang et al.

(10) Patent No.: US 12,295,801 B2
(45) Date of Patent: May 13, 2025

(54) METHOD AND SYSTEM FOR EVALUATING IMPLANTING PRECISION OF AN IMPLANT

(71) Applicant: BEIJING YAKEBOT TECHNOLOGY CO., LTD, Beijing (CN)

(72) Inventors: Lifeng Wang, Beijing (CN); Chen Shen, Beijing (CN)

(73) Assignee: BEIJING YAKEBOT TECHNOLOGY CO., LTD, Beijing (CN)

(*) Notice: Subject to any disclaimer, the term of this patent is extended or adjusted under 35 U.S.C. 154(b) by 828 days.

(21) Appl. No.: 17/267,262

(22) PCT Filed: May 6, 2019

(86) PCT No.: PCT/CN2019/085680
§ 371 (c)(1),
(2) Date: Feb. 9, 2021

(87) PCT Pub. No.: WO2020/034668
PCT Pub. Date: Feb. 20, 2020

(65) Prior Publication Data
US 2021/0307882 A1 Oct. 7, 2021

(30) Foreign Application Priority Data
Aug. 15, 2018 (CN) .......................... 201810931225.7

(51) Int. Cl.
*A61C 13/00* (2006.01)
*A61B 34/10* (2016.01)
*A61C 8/00* (2006.01)

(52) U.S. Cl.
CPC .......... *A61C 13/0004* (2013.01); *A61B 34/10* (2016.02); *A61C 8/00* (2013.01); *A61B 2034/105* (2016.02); *A61B 2034/108* (2016.02)

(58) Field of Classification Search
CPC ....... A61C 13/0004; A61C 8/00; A61B 34/10; A61B 2034/105; A61B 2034/108
See application file for complete search history.

(56) References Cited

U.S. PATENT DOCUMENTS 6,319,006 B1 * 11/2001 Scherer .................. A61C 1/084
433/215
8,562,338 B2 * 10/2013 Kitching .................. A61C 7/08
433/24

(Continued)

FOREIGN PATENT DOCUMENTS

| CN | 102293682 A | 12/2011 |
| CN | 104042352 A | 9/2014 |

(Continued)

OTHER PUBLICATIONS

International Search Report for corresponding International application No. PCT/CN2019/085680; dated Jul. 24, 2019 (2 pages).

(Continued)

*Primary Examiner* — Nicholas D Lucchesi
*Assistant Examiner* — Hao D Mai
(74) *Attorney, Agent, or Firm* — Faegre Drinker Biddle & Reath LLP (57) ABSTRACT

Embodiments of the present application provides a method and a system for evaluating implanting precision of an implant. The method includes: obtaining a second surface model of an oral cavity containing a target implant; obtaining an actual position of the target implant in a first three-dimensional model based on the second surface model, the first three-dimensional model and a first surface model; and obtaining an evaluation result of the implanting precision of the target implant based on the actual position of the target implant in the first three-dimensional model and an predicted position of the target implant in the first three-dimensional model. By means of the method and system (Continued)

according to the embodiments of the present application, the second surface model of the oral cavity containing the target implant is obtained after implantation is completed using an oral digital scanning device to obtain the evaluation result of the implanting precision of an implant of the target implant. More accurate evaluation result of implant can be obtained due to the elimination of metallic implant artifacts in the obtained secondary surface model as compared to the three-dimensional digital model obtained based on CT device in the prior art.

15 Claims, 3 Drawing Sheets

(56) References Cited

U.S. PATENT DOCUMENTS

| | | | | |
|---|---|---|---|---|
| 8,591,225 B2* | 11/2013 | Wu | | A61C 7/002 |
| | | | | 382/128 |
| 2002/0102517 A1 | 8/2002 | Poirier | | |
| 2005/0084144 A1* | 4/2005 | Feldman | | A61B 6/5258 |
| | | | | 382/128 |
| 2006/0105291 A1* | 5/2006 | Stein | | B23B 47/28 |
| | | | | 433/75 |
| 2009/0092948 A1* | 4/2009 | Gantes | | A61C 1/084 |
| | | | | 433/215 |
| 2010/0128033 A1 | 5/2010 | Stevens et al. | | |
| 2011/0033819 A1* | 2/2011 | Freyer | | A61C 1/084 |
| | | | | 433/72 |
| 2014/0234803 A1* | 8/2014 | Hehn | | A61C 9/0053 |
| | | | | 433/214 |
| 2015/0150655 A1* | 6/2015 | Frank | | A61B 6/5247 |
| | | | | 433/29 |
| 2016/0038092 A1* | 2/2016 | Golay | | A61C 8/00 |
| | | | | 600/408 |
| 2016/0374780 A1 | 12/2016 | Carrillo Gonzalez et al. | | |
| 2017/0049544 A1* | 2/2017 | Stevens | | A61B 5/7425 |
| 2021/0015590 A1* | 1/2021 | Sharou | | A61C 8/0001 |

FOREIGN PATENT DOCUMENTS

| | | |
|---|---|---|
| CN | 104271067 A | 1/2015 |
| CN | 105078596 A | 11/2015 |
| CN | 105287039 A | 2/2016 |
| CN | 107260343 A | 10/2017 |
| CN | 107485460 A | 12/2017 |
| CN | 107661159 A | 2/2018 |
| CN | 107742530 A | 2/2018 |
| CN | 108269247 A | 7/2018 |
| CN | 108986209 A | 12/2018 |
| KR | 101870901 B1 | 7/2018 |

OTHER PUBLICATIONS

Flügge, Tabea V., et al. "Precision of Dental Implant Digitization Using Intraoral Scanners." The International Journal of Prosthodontics 29.3 (2016): 277-283.

Guo, Qiuyun et al. "Clinical accuracy evaluation of CAD/CAM dental implant guides combined with 3D laser scanning." Journal of Clinical Dentistry, vol. 1 Issue 3-6, (2014). Abstract, Machine Translation.

* cited by examiner

METHOD AND SYSTEM FOR EVALUATING IMPLANTING PRECISION OF AN IMPLANT

CROSS-REFERENCE TO RELATED APPLICATION

The present application claims priority to Chinese Application No. 2018109312257 filed on Aug. 15, 2018, entitled "Method and System for Evaluating Implanting Precision of an Implant," which is hereby incorporated by reference in its entirety.

FIELD OF TECHNOLOGY

The present application relates to the technical field of medical treatment, and more particularly, to a method and a system for evaluating implanting precision of an implant.

BACKGROUND

At present, a commonly used method for evaluating the implanting precision of an implant includes obtaining the two-dimensional information about the implant recipient's jaw through computed tomography (CT) before implantation, and then reconstructing a three-dimensional digital model of the jaw based on the two-dimensional information of the jaw and performing preoperative planning so as to determine the optimum implant placement of the implant; performing a secondary CT scan after the implantation to reconstruct the three-dimensional digital model of the implant recipient's jaw and obtaining the implanting precision of the implant according to the three-dimensional digital models of the jaw scanned before and after the operation.

However, implants are generally made of metal, the X-rays emitted by CT scans will be greatly attenuated when they pass through the metal, and thus the tissue images behind the metal will not be well recorded, resulting in artifacts that affect the accuracy of the evaluation result of the implanting precision.

SUMMARY

Embodiments of the present application provide a method and a system for evaluating implanting precision of an implant to solve the problem of large error in the evaluation result of implanting precision of an implant in the prior art, and improve the accuracy of the evaluation result of implanting precision of an implant.

An embodiment of the present application provides a method for evaluating implanting precision of an implant, including:
  obtaining a second surface model of an oral cavity containing a target implant;
  obtaining an actual position of the target implant in a first three-dimensional model based on the second surface model, the first three-dimensional model and a first surface model; and
  obtaining an evaluation result of the implanting precision of the target implant based on the actual position of the target implant in the first three-dimensional model and a predicted position of the target implant in the first three-dimensional model;
  wherein the first three-dimensional model is an entity model that represents information about teeth in the oral cavity without the target implant, the first surface model is a surface model that represents information about teeth in the oral cavity without the target implant, and the second surface model is a surface model that represents information about teeth in the oral cavity containing the target implant.

An embodiment of the present application provides a system for evaluating implanting precision of an implant, including:
  a model acquirer, configured to obtain a second surface model of an oral cavity containing a target implant;
  an actual position acquirer, configured to obtain an actual position of the target implant in a first three-dimensional model based on the second surface model, the first three-dimensional model and a first surface model; and
  an evaluation result acquirer, configured to obtain an evaluation result of the implanting precision of the target implant based on the actual position of the target implant in the first three-dimensional model and a predicted position of the target implant in the first three-dimensional model;
  wherein the first three-dimensional model is an entity model that represents information about teeth in the oral cavity without the target implant, the first surface model is a surface model that represents information about teeth in the oral cavity without the target implant, and the second surface model is a surface model that represents information about teeth in the oral cavity containing the target implant.

An embodiment of the present application provides an electronic device, comprising a memory and a processor, wherein the processor and the memory communicate with each other through a bus; the memory stores program instructions executable by the processor, and the processor calls the program instructions to perform the method mentioned above.

An embodiment of the present application provides a non-transitory computer readable storage medium, storing computer instructions that cause a computer to perform the method mentioned above.

By means of the method and system according to the embodiments of the present application, the second surface model of the oral cavity containing the target implant is obtained after implantation is completed using an oral digital scanning device to obtain the evaluation result of the implanting precision of the target implant based on the second surface model, as well as the first three-dimensional model and the first surface model obtained before implantation. Since the obtained second surface model is clearer and contains more information than the three-dimensional digital model obtained based on CT device in the prior art, it is possible to obtain more accurate evaluation result of implanting precision of an implant.

BRIEF DESCRIPTION OF THE DRAWINGS

In order to make the technical solutions in the embodiments of the present application or the prior art clearer, drawings needed in the embodiments or the description of the prior art is briefly introduced as follows. Obviously, the drawings in the following description are only some of the embodiments of the present application. For those of ordinary skill in the art, other drawings can be obtained based on these drawings without paying any creative effort.

DETAILED DESCRIPTION

In order to specify the objectives, technical solutions and advantages of the embodiments of the present application, the technical solutions in the embodiments of the present application will be described clearly and completely in conjunction with the accompanying drawings in the embodiments of the present application. Obviously, the embodiments described below are part of the embodiments of the present application, rather than all of the embodiments. Based on the embodiments in the present application, all other embodiments obtained by those of ordinary skill in the art without creative effort shall fall within the protection scope of the present application.

Figure 1:
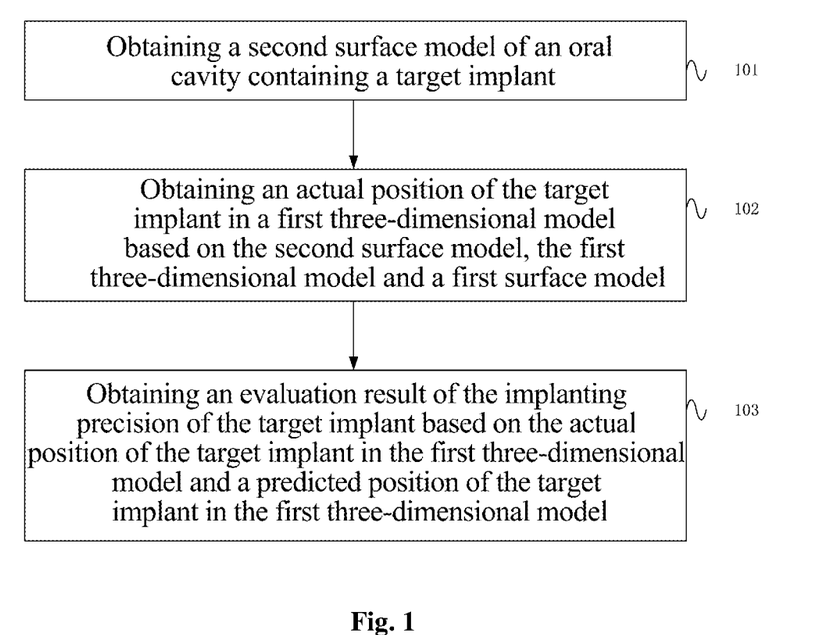
FIG. 1 is a flowchart of a method for evaluating implanting precision of an implant according to an embodiment of the present application.

FIG. 1 is a flowchart of a method for evaluating implanting precision of an implant according to an embodiment of the present application. As shown in FIG. 1, the method includes:

S101, obtaining a second surface model of an oral cavity containing a target implant;

S102, obtaining an actual position of the target implant in a first three-dimensional model based on the second surface model, the first three-dimensional model and a first surface model; and S103, obtaining an evaluation result of the implanting precision of the target implant based on the actual position of the target implant in the first three-dimensional model and a predicted position of the target implant in the first three-dimensional model;

wherein the first three-dimensional model is an entity model that represents information about teeth in the oral cavity without the target implant, the first surface model is a surface model that represents information about teeth in the oral cavity without the target implant, and the second surface model is a surface model that represents information about teeth in the oral cavity containing the target implant.

Specifically, for S101, the implant is also called an oral implant. Prior to implantation for the implant recipient, there may be several implants in the oral cavity. Therefore, in the embodiment of the present application, the implant to be evaluated for implanting precision is called the target implant. A second surface model of an oral cavity containing the target implant is obtained based on an oral digital scanning device, wherein the oral digital scanning device is an intraoral scanner, and the second surface model is a surface model containing information about teeth obtained by scanning the oral cavity containing the target implant through the intraoral scanner. It should be noted that S101 is performed after implantation. The information about teeth specifically refers to the arrangement information, size information and defect information about the teeth.

For S102, before implantation, the first three-dimensional model of the oral cavity without the target implant is obtained based on the CT scanning device, and the first surface model of the oral cavity without the target implant is obtained based on the oral digital scanning device. The oral scanning device, which has been introduced above, is configured to obtain an oral surface model before implantation, which is referred herein as the first surface model. The first surface model is a surface model that represents information about teeth in the oral cavity without the target implant, the CT scanning device is a device manufactured based on computer tomography, and the first three-dimensional model is a three-dimensional digital model reconstructed from the two-dimensional information of the jaw obtained by the CT scanning device, and represents an entity model of the information about teeth in the oral cavity without the target implant. The actual position of the target implant in the second surface model in the first three-dimensional model is obtained based on the second surface model, the first three-dimensional model and the first surface model.

For S103, in order to evaluate the implanting precision of an implant of the implanted target implant, it is necessary to compare the predicted position of the target implant before implantation with the actual position of the target implant after implantation, and then obtain the evaluation result of the implanting precision of the target implant. In an embodiment, the predicted position refers to a predicted optimal spatial area where a target implant should be implanted before implantation, and the actual position refers to the spatial area where the target implant is located after implantation.

By means of the method according to the embodiment of the present application, the second surface model of the oral cavity containing the target implant is obtained after implantation is completed using an oral digital scanning device to obtain the evaluation result of the implanting precision of the target implant based on the second surface model, as well as the first three-dimensional model and the first surface model obtained before implantation. Since the obtained second surface model is clearer and contains more information than the three-dimensional digital model obtained based on CT device in the prior art, the evaluation result of implanting precision of an implant is more precise.

Figure 2:
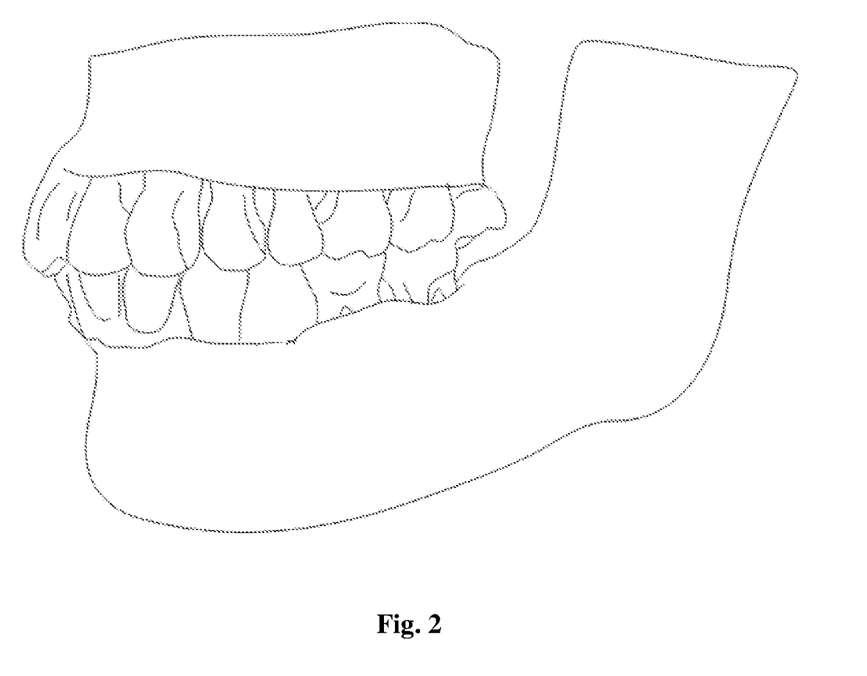
FIG. 2 is a schematic diagram of a first three-dimensional model according to an embodiment of the present application.
Figure 3:
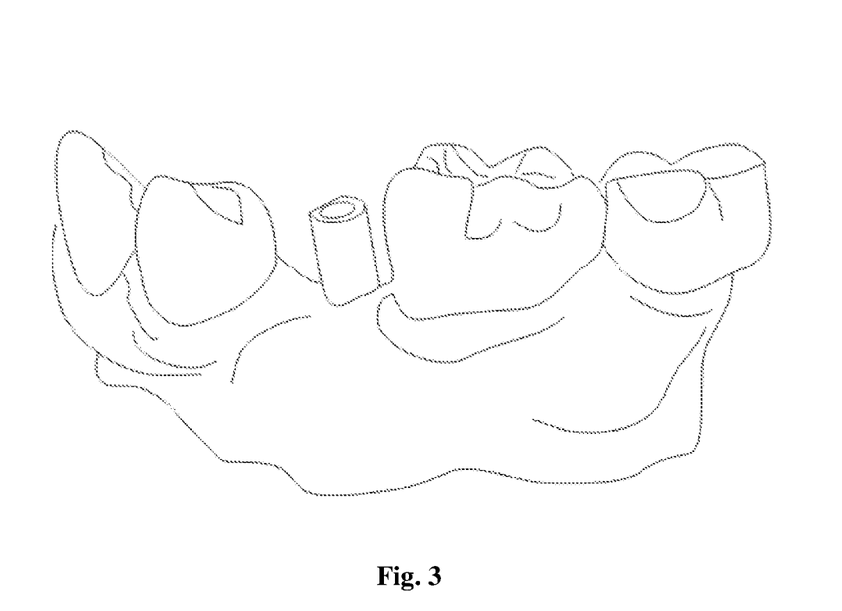
FIG. 3 is a schematic diagram of a second surface model according to an embodiment of the present application.

As an optional embodiment, on the basis of the forgoing embodiment, an embodiment of the present application illustrates the first three-dimensional model and the second surface model in the forgoing embodiment by means of drawings. FIG. 2 is a schematic diagram of a first three-dimensional model according to an embodiment of the present application. As shown in FIG. 2, this model shows the arrangement of teeth in the oral cavity of the implant recipient. FIG. 3 is a schematic diagram of a second surface model according to an embodiment of the present application. As shown in FIG. 3, an implant is placed in the tooth-missing position of the implant recipient, what is visible to the naked eye is the abutment part, and the implant is located in the alveolar bone below the abutment.

On the basis of the foregoing embodiments, before the obtaining an actual position of the target implant in a first three-dimensional model based on the second surface model, the first three-dimensional model and a first surface model, the method further includes:

obtaining a scanning result of the oral cavity without the target implant based on a CT scanning device;

constructing the first three-dimensional model based on the scanning result; and obtaining a scanning result of the oral cavity without the target implant as the first surface model based on an oral digital scanning device.

Specifically, the embodiment of the present application is a process of obtaining the first three-dimensional model and the first surface model before implantation. In an embodiment, the first three-dimensional model is reconstructed based on the two-dimensional information of the jaw scanned by the CT scanning device, and the first surface model is obtained from the scanning of the oral scanning device.

On the basis of the foregoing embodiments, the obtaining an actual position of the target implant in a first three-dimensional model based on the second surface model, the first three-dimensional model and a first surface model further includes:
registering the first surface model with the first three-dimensional model, and registering the second surface model with the first surface model; and
obtaining the actual position of the target implant in the first three-dimensional model according to a registered second surface model and a standard implant abutment model.

Specifically, model registration is the process of matching and superimposing multiple models acquired at different times, with different imaging devices or under different conditions (weather, illuminance, camera position and angle, etc.). For the two models to be registered, the registration process is as follows: performing feature extraction on the two models to obtain feature points; finding out matched feature point pairs by performing similarity measurement; obtaining spatial coordinate transformation parameters of the model through the matching feature point pairs; and performing the model registration by the coordinate transformation parameters.

Specifically, for the process of registering the first surface model with the first three-dimensional model, the feature points on the tooth surfaces of the two models are selected separately, and then the two models are roughly registered based on the registration process, so that the distance between the two models is less than a first preset threshold. Then, the two models are precisely registered based on the ICP algorithm, so that the distance between the two models is less than a second preset threshold. It should be noted that the second preset threshold is less than the first preset threshold value, and the first preset threshold and the second preset threshold are set according to specific scenarios, which are not specifically defined in the embodiment of the present application. In an embodiment, the ICP algorithm is a point-set-to-point-set registration method.

The process of registering the second surface model with the first surface model is similar to the process of registering the first surface model with the first three-dimensional model, and thus will not be repeated here.

The top of the implanted implant is connected to the abutment, and the dental crown is covered around the abutment. Since only the abutment part can be displayed in the registered second surface model, it is necessary to register the standard implant abutment model with the abutment part of the registered second surface model to take the spatial area of the implant in the registered standard implant abutment model as the actual position of the target implant. It should be noted that the standard implant abutment model includes two parts: the implant and the abutment.

On the basis of the foregoing embodiments, before the obtaining an evaluation result of the accuracy of the target implant based on the actual position of the target implant in the first three-dimensional model and a predicted position of the target implant in the first three-dimensional model, the method further includes:
determining an initial predicted position of the target implant in the first three-dimensional model based on the first three-dimensional model; and
obtaining shape parameters of teeth adjacent to the target implant based on the first surface model to correct the initial predicted position so as to obtain the predicted position of the target implant in the first three-dimensional model.

Specifically, the embodiment of the present application is a process of obtaining the predicted position of the target implant as follows: the initial predicted position of the target implant in the first three-dimensional model is determined according to the first three-dimensional model reconstructed from the three-dimensional information of the jaw obtained by the CT device. The dental crown must be connected to the abutment after the implant is implanted, and for the design of the dental crown, the shape of the teeth adjacent to the target implant needs to be considered. In addition, the initial predicted position of the implant needs to be fine-tuned in the process of considering the shape of the teeth adjacent to the target implant to design the dental crown. Therefore, the shape parameters of the teeth adjacent to the target implant can be obtained according to the first surface model scanned by the oral scanning device to correct the initial predicted position so as to obtain the predicted position of the target implant in the first three-dimensional model.

On the basis of the foregoing embodiments, the obtaining an evaluation result of the accuracy of the target implant based on the actual position of the target implant in the first three-dimensional model and a predicted position of the target implant in the first three-dimensional model further includes:
obtaining a shoulder deviation, a root deviation and an angular deviation of the target implant based on the actual position of the target implant in the first three-dimensional model and the predicted position of the target implant in the first three-dimensional model; and
obtaining the evaluation result of the implanting precision of the target implant based on the shoulder deviation, the root deviation and the angular deviation of the target implant.

Specifically, shoulder deviation, root deviation and angular deviation are all indicators used to evaluate the implanting precision of an implant. In an embodiment, the shoulder deviation is the deviation between shoulder feature points in an actual position and shoulder feature points in a predicted position, the root deviation is the deviation between root feature points in the actual position and root feature points in the predicted position, and the angular deviation is the angular deviation between the predicted position and the actual position when the two are each considered as a whole.

On the basis of the foregoing embodiments, the obtaining a shoulder deviation, a root deviation and an angular deviation of the target implant based on the actual position of the target implant in the first three-dimensional model and the predicted position of the target implant in the first three-dimensional model further includes:
fitting the actual position and the predicted position respectively using regular bodies of revolution based on the actual position of the target implant in the first three-dimensional model and the predicted position of the target implant in the first three-dimensional model to obtain an actual fitted body of revolution and a predicted fitted body of revolution;

obtaining actual shoulder feature points and actual root feature points based on the actual fitted body of revolution, and obtaining predicted shoulder feature points and predicted root feature points based on the predicted fitted body of revolution; and obtaining the shoulder deviation of the target implant based on the actual shoulder feature points and the predicted shoulder feature points, obtaining the root deviation of the target implant based on the actual root feature points and predicted root feature points, and obtaining the angular deviation of the target implant based on the actual shoulder feature points, the actual root feature points, the predicted shoulder feature points and the predicted root feature points.

Specifically, a regular cylinder is used to respectively fit the predicted position and the actual position to obtain the actual regular cylinder (i.e., the actual fitted body of revolution) and the predicted regular cylinder (i.e., the predicted fitted body of revolution). The centers of the upper and lower bottom surfaces of the actual regular cylinder are taken as the actual shoulder feature point $h_a$ and the actual root feature point aa of the target implant, respectively. The same method is used to obtain the predicted shoulder feature point $h_p$ and the predicted root feature point $a_p$ of the target implant.

Figure 4:
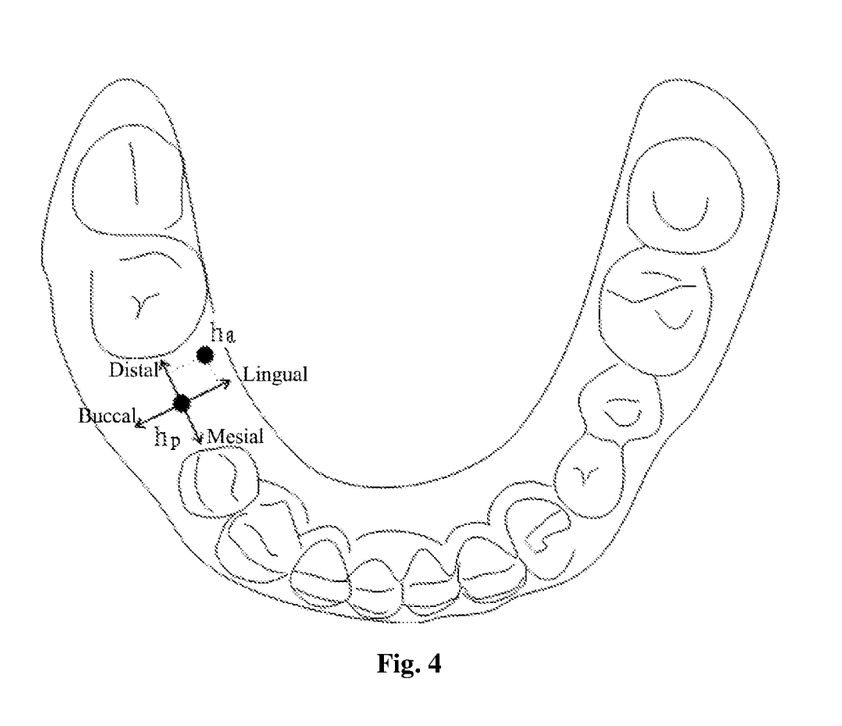
FIG. 4 is a schematic diagram of a method for calculating shoulder deviation according to an embodiment of the present application.

Taking the process of obtaining the shoulder deviation as an example, FIG. 4 is a schematic diagram of a method for calculating shoulder deviation according to an embodiment of the present application. As shown in FIG. 4, a reference coordinate system for the buccal-lingual and mesial-distal directions is established using the predicted shoulder feature point $h_p$ of the target implant as the origin. The difference between the actual shoulder feature point $h_a$ and the predicted shoulder feature point $h_p$ in the buccal-lingual and the mesial-distal directions can be calculated according to the coordinates of the three-dimensional spatial points. Wherein the actual shoulder feature point of the target implant in FIG. 4 is deviated to the lingual and distal directions.

It should be noted that for the shoulder and root of the implant, the horizontal deviation in the buccal-lingual and the mesial-distal directions, and the vertical depth error can be shown respectively. The mesial refers to the direction proximate to the midline of the face, and the distal refers to the direction further away. The buccal refers to the side of the tooth surface that tilts toward the cheek, and the lingual refers to the side of the tooth surface that tilts toward the tongue.

The angular deviation θ can be directly calculated according to the angle formula of two straight lines:

$$\theta = \cos\langle h_p\vec{a}_p, h_a\vec{a}_a\rangle = \frac{\|h_p\vec{a}_p \Box h_a\vec{a}_a\|}{\|h_p\vec{a}_p\|\|\Box\|\|h_a\vec{a}_a\|}$$

On the basis of the foregoing embodiments, the obtaining the evaluation result of the implanting precision of an implant of the target implant based on the shoulder deviation, the root deviation and the angular deviation of the target implant further includes:

performing weighted calculation on the shoulder deviation, the root deviation and the angular deviation according to a weight of the shoulder deviation, a weight of the root deviation and a weight of the angular deviation; and comparing the result of the weighted calculation with a preset threshold interval to obtain the evaluation result of the implanting precision of an implant of the target implant.

It should be noted that the weight of the shoulder deviation, the weight of the root deviation, the weight of the angular deviation, and the preset threshold interval can be set according to specific scenarios, which are not specifically defined in the embodiment of the present application.

An embodiment of the present application provides a system for evaluating implanting precision of an implant, including:

a model acquirer, configured to obtain a second surface model of an oral cavity containing a target implant;

an actual position acquirer, configured to obtain an actual position of the target implant in a first three-dimensional model based on the second surface model, the first three-dimensional model and a first surface model; and an evaluation result acquirer, configured to obtain an evaluation result of the implanting precision of the target implant based on the actual position of the target implant in the first three-dimensional model and a predicted position of the target implant in the first three-dimensional model;

wherein the first three-dimensional model is obtained based on an CT scanning device before implantation, the first surface model is obtained based on an oral digital scanning device before implantation, and the second surface model is obtained based on an oral digital scanning device after implantation.

It should be noted that the system of the embodiment of the present application can be configured to implement the technical solution of the embodiments of the method for evaluating implanting precision of an implant shown in FIG. 1, the principles and technical effects of which are similar and thus will not be repeated here.

In summary, by means of the method and system according to the embodiments of the present application, the second surface model of the oral cavity containing the target implant is obtained after implantation is completed using an oral digital scanning device to obtain the evaluation result of the implanting precision of the target implant based on the second surface model, as well as the first three-dimensional model and the first surface model obtained before implantation. Since the obtained second surface model is clearer and contains more information than the three-dimensional digital model obtained based on CT device in the prior art, it is possible to obtain more accurate evaluation result of implanting precision of an implant. Moreover, by obtaining the shoulder deviation, the root deviation and the angular deviation of the target implant, the evaluation of implanting precision of an implant is more complete and precise.

Figure 5:
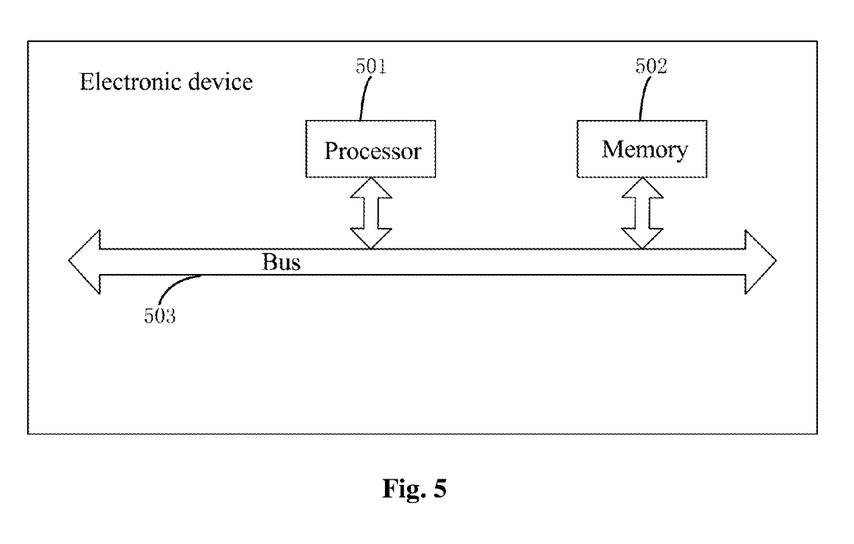
FIG. 5 is a structural block diagram of an electronic device according to an embodiment of the present application.

FIG. 5 is a structural block diagram of an electronic device according to an embodiment of the present application. As shown in FIG. 5, the device includes: a processor 501, a memory 502 and a bus 503, wherein the processor 501 and the memory 502 communicate with each other through the bus 503. The processor 501 is configured to call the program instructions in the memory 502 to perform the methods provided in the foregoing method embodiments, for example, including: obtaining a second surface model of an oral cavity containing a target implant; obtaining an actual position of the target implant in a first three-dimensional model based on the second surface model, the first three-dimensional model and a first surface model; and obtaining an evaluation result of the implanting precision of the target implant based on the actual position of the target implant in the first three-dimensional model and an predicted position of the target implant in the first three-dimensional model.

An embodiment of the present application discloses a computer program product, including a computer program stored on a non-transitory computer readable storage medium, wherein the computer program includes program instructions, and the computer can perform, when performing the program instructions, the methods provided in the foregoing method embodiments, for example, including: obtaining a second surface model of an oral cavity containing a target implant; obtaining an actual position of the target implant in a first three-dimensional model based on the second surface model, the first three-dimensional model and a first surface model; and obtaining an evaluation result of the implanting precision of the target implant based on the actual position of the target implant in the first three-dimensional model and an predicted position of the target implant in the first three-dimensional model.

An embodiment of the present application provides a non-transitory computer readable storage medium, storing computer instructions that cause a computer to perform the methods provided in the foregoing method embodiments, for example, including: obtaining a second surface model of an oral cavity containing a target implant; obtaining an actual position of the target implant in a first three-dimensional model based on the second surface model, the first three-dimensional model and a first surface model; and obtaining an evaluation result of the accuracy of the target implant based on the actual position of the target implant in the first three-dimensional model and an predicted position of the target implant in the first three-dimensional model.

It can be understood by those of ordinary skill in the art that all or part of the steps of implementing the method embodiments above may be completed by using hardware related to the program instructions. The foregoing program may be stored in a computer readable storage medium, and the program performs foregoing steps including the method embodiments above when being executed. The foregoing storage medium includes: a medium that can store program codes, such as a ROM, a RAM, a magnetic disc, or a compact disc.

Through the description of the embodiments above, those skilled in the art can clearly understand that the various embodiments can be implemented by means of software and a necessary general hardware platform, and of course, by hardware. Based on such understanding, the technical solution of the present application or a part of the technical solution, which is essential or contributes to the prior art, may be embodied in the form of a software product, which is stored in a storage medium such as ROM/RAM, magnetic discs, compact discs, etc., including several instructions to cause a computer device (for example, a personal computer, server, or network device, etc.) to perform various embodiments or a part of the methods described in various embodiments.

It should be noted that the embodiments are only for illustrating the technical solutions of the present application, rather than limiting them; although the present application has been described in detail with reference to the foregoing embodiments, those skilled in the art should understand that the technical solutions documented in the preceding embodiments may still be modified, or parts of the technical features thereof can be equivalently substituted; and such modifications or substitutions do not deviate from scope of the technical solutions of the embodiments of the present application.

The invention claimed is:

1. A method for evaluating implanting precision, applied to a system for evaluating implanting precision, comprising:
   using a computed tomography scanning device to scan an oral cavity, before implantation, to acquire a two-dimensional scan of the oral cavity;
   constructing a first three-dimensional model of the oral cavity, based on the two-dimensional scan;
      wherein the first three-dimensional model is an entity model that represents information about teeth in the oral cavity without a target implant;
   using an oral digital scanning device to scan the oral cavity, before implantation, to produce a first surface model of the oral cavity;
      wherein the first surface model is a surface model that represents information about the teeth in the oral cavity without the target implant;
   identifying a predicted position of the target implant in the first three-dimensional model, comprising:
      determining an initial predicted position of the target implant in the first three-dimensional model; and
      obtaining shape parameters of teeth adjacent to the target implant based on the first surface model to correct the initial predicted position, so as to obtain the predicted position of the target implant in the first three-dimensional model;
   using the oral digital scanning device to scan the oral cavity, after implantation is completed, to produce a second surface model of the oral cavity comprising the target implant;
      wherein the second surface model is a surface model that represents information about the teeth in the oral cavity with the target implant located therein,
   determining an actual position of the target implant in the first three-dimensional model, based on the second surface model, the first three-dimensional model and the first surface model; and
   comparing the actual position of the target implant in the first three-dimensional model and the predicted position of the target implant in the first three-dimensional model to determine an evaluation result of the implanting precision of the target implant.

2. The method of claim 1, wherein the determining of the actual position of the target implant in the first three-dimensional model comprises:
   registering the first surface model with the first three-dimensional model by matching and superimposing the first surface model and the first three-dimensional model to form a registered first surface model,
   registering the second surface model with the registered first surface model by matching and superimposing the second surface model with the registered first surface model to acquire a registered second surface model; and
   registering the registered second surface model with a standard implant abutment model.

3. The method of claim 1, wherein the evaluation result is determined from a shoulder deviation, a root deviation and an angular deviation of the target implant based on the actual position of the target implant in the first three-dimensional model and the predicted position of the target implant in the first three-dimensional model.

4. The method of claim 3, wherein the shoulder deviation, the root deviation and the angular deviation are determined by
fitting the actual position and the predicted position respectively using regular bodies of revolution based on the actual position of the target implant in the first three-dimensional model and the predicted position of the target implant in the first three-dimensional model to obtain an actual fitted body of revolution and a predicted fitted body of revolution;
obtaining actual shoulder feature points and actual root feature points based on the actual fitted body of revolution, and obtaining predicted shoulder feature points and predicted root feature points based on the predicted fitted body of revolution; and
obtaining the shoulder deviation of the target implant based on the actual shoulder feature points and the predicted shoulder feature points, obtaining the root deviation of the target implant based on the actual root feature points and predicted root feature points, and obtaining the angular deviation of the target implant based on the actual shoulder feature points, the actual root feature points, the predicted shoulder feature points and the predicted root feature points.

5. The method of claim 3, wherein the evaluation result is determined by
performing a weighted calculation on the shoulder deviation, the root deviation and the angular deviation based on a weight of the shoulder deviation, a weight of the root deviation and a weight of the angular deviation; and
comparing the result of the weighted calculation with a preset threshold interval.

6. A system for evaluating implanting precision, comprising: a computer including a non-transitory computer readable storage medium having computer readable program codes stored thereon, the computer being configured to execute operations:
using a computed tomography scanning device to scan an oral cavity, before implantation, to acquire a two-dimensional scan of the oral cavity;
constructing a first three-dimensional model of the oral cavity, based on the two-dimensional scan;
wherein the first three-dimensional model is an entity model that represents information about teeth in the oral cavity without a target implant;
using an oral digital scanning device to scan the oral cavity, before implantation, to produce a first surface model of the oral cavity;
wherein the first surface model is a surface model that represents information about the teeth in the oral cavity without the target implant;
identifying a predicted position of the target implant in the first three-dimensional model, comprising:
determining an initial predicted position of the target implant in the first three-dimensional model; and
obtaining shape parameters of teeth adjacent to the target implant based on the first surface model to correct the initial predicted position, so as to obtain the predicted position of the target implant in the first three-dimensional model;
using the oral digital scanning device to scan the oral cavity, after implantation is completed, to produce a second surface model of the oral cavity comprising the target implant;
wherein the second surface model is a surface model that represents information about the teeth in the oral cavity with the target implant located therein,
determining an actual position of the target implant in the first three-dimensional model, based on the second surface model, the first three-dimensional model and the first surface model; and
comparing the actual position of the target implant in the first three-dimensional model and the predicted position of the target implant in the first three-dimensional model to determine an evaluation result of the implanting precision of the target implant.

7. The system of claim 6, wherein the determining of the actual position of the target implant in the first three-dimensional model, comprises:
registering the first surface model with the first three-dimensional model by matching and superimposing the first surface model and the first three-dimensional model to form a registered first surface model,
registering the second surface model with the registered first surface model by matching and superimposing the second surface model with the registered first surface model to acquire a registered second surface model; and
registering the registered second surface model with a standard implant abutment model.

8. The system of claim 6, wherein the evaluation result is determined from a shoulder deviation, a root deviation and an angular deviation of the target implant based on the actual position of the target implant in the first three-dimensional model and the predicted position of the target implant in the first three-dimensional model.

9. The system of claim 8, wherein the shoulder deviation, the root deviation and the angular deviation are determined by
fitting the actual position and the predicted position respectively, using regular bodies of revolution based on the actual position of the target implant in the first three-dimensional model and the predicted position of the target implant in the first three-dimensional model to obtain an actual fitted body of revolution and a predicted fitted body of revolution;
obtaining actual shoulder feature points and actual root feature points based on the actual fitted body of revolution, and obtaining predicted shoulder feature points and predicted root feature points based on the predicted fitted body of revolution; and
obtaining the shoulder deviation of the target implant based on the actual shoulder feature points and the predicted shoulder feature points, obtaining the root deviation of the target implant based on the actual root feature points and predicted root feature points, and obtaining the angular deviation of the target implant based on the actual shoulder feature points, the actual root feature points, the predicted shoulder feature points and the predicted root feature points.

10. The system of claim 8, wherein the evaluation result is determined by
performing a weighted calculation on the shoulder deviation, the root deviation and the angular deviation based on a weight of the shoulder deviation, a weight of the root deviation and a weight of the angular deviation; and
comparing the result of the weighted calculation with a preset threshold interval.

11. An electronic device, comprising a memory and a processor, wherein the processor and the memory communicate with each other through a bus; the memory stores program instructions executable by the processor, and the processor calls the program instructions to perform operations:

using a computed tomography scanning device to scan an oral cavity, before implantation, to acquire a two-dimensional scan of the oral cavity;

constructing a first three-dimensional model of the oral cavity, based on the two-dimensional scan;

wherein the first three-dimensional model is an entity model that represents information about teeth in the oral cavity without a target implant;

using an oral digital scanning device to scan the oral cavity, before implantation, to produce a first surface model of the oral cavity;

wherein the first surface model is a surface model that represents information about the teeth in the oral cavity without the target implant;

identifying a predicted position of the target implant in the first three-dimensional model, comprising:

determining an initial predicted position of the target implant in the first three-dimensional model; and         obtaining shape parameters of teeth adjacent to the target implant based on the first surface model to correct the initial predicted position, so as to obtain the predicted position of the target implant in the first three-dimensional model;

using the oral digital scanning device to scan the oral cavity, after implantation is completed, to produce a second surface model of the oral cavity comprising the target implant;

wherein the second surface model is a surface model that represents information about the teeth in the oral cavity with the target implant located therein,     determining an actual position of the target implant in the first three-dimensional model, based on the second surface model, the first three-dimensional model and the first surface model; and     comparing the actual position of the target implant in the first three-dimensional model and the predicted position of the target implant in the first three-dimensional model to determine an evaluation result of the implanting precision of the target implant.

12. The electronic device of claim 11, wherein the determining of the actual position of the target implant in the first three-dimensional model, comprises:

registering the first surface model with the first three-dimensional model by matching and superimposing the first surface model and the first three-dimensional model to form a registered first surface model,     registering the second surface model with the registered first surface model by matching and superimposing the second surface model with the registered first surface model to acquire a registered second surface model; and     registering the registered second surface model with a standard implant abutment model.

13. The electronic device of claim 11, wherein the evaluation result is determined from a shoulder deviation, a root deviation and an angular deviation of the target implant based on the actual position of the target implant in the first three-dimensional model and the predicted position of the target implant in the first three-dimensional model.

14. The electronic device of claim 13, wherein the shoulder deviation, the root deviation and the angular deviation are determined by     fitting the actual position and the predicted position respectively using regular bodies of revolution based on the actual position of the target implant in the first three-dimensional model and the predicted position of the target implant in the first three-dimensional model to obtain an actual fitted body of revolution and a predicted fitted body of revolution;

obtaining actual shoulder feature points and actual root feature points based on the actual fitted body of revolution, and obtaining predicted shoulder feature points and predicted root feature points based on the predicted fitted body of revolution; and     obtaining the shoulder deviation of the target implant based on the actual shoulder feature points and the predicted shoulder feature points, obtaining the root deviation of the target implant based on the actual root feature points and predicted root feature points, and obtaining the angular deviation of the target implant based on the actual shoulder feature points, the actual root feature points, the predicted shoulder feature points and the predicted root feature points.

15. The electronic device of claim 13, wherein the evaluation result is determined by     performing a weighted calculation on the shoulder deviation, the root deviation and the angular deviation based on a weight of the shoulder deviation, a weight of the root deviation and a weight of the angular deviation; and     comparing the result of the weighted calculation with a preset threshold interval.

\* \* \* \* \*